United States Patent [19]

Gilvarg et al.

[11] 4,427,582

[45] Jan. 24, 1984

[54] ANTIMICROBIAL DISULFIDE PRODRUGS

[75] Inventors: Charles Gilvarg, Princeton, N.J.; William D. Kingsbury, King of Prussia, Pa.

[73] Assignee: SmithKline Beckman Corporation, Philadelphia, Pa.

[21] Appl. No.: 386,365

[22] Filed: Jun. 8, 1982

[51] Int. Cl.$^3$ .................... C07C 103/52; A61K 37/00
[52] U.S. Cl. ............................. 260/112.5 R; 424/177
[58] Field of Search .................. 424/177; 260/112.5 R

[56] References Cited

U.S. PATENT DOCUMENTS 4,237,267 12/1980 Okuyama et al. .
4,258,193 3/1981 Fujii et al. .
4,284,624 8/1981 Natarajan et al. .
4,325,943 4/1982 Natarajan et al. .
4,325,944 4/1982 Natarajan et al. .
4,325,945 4/1982 Natarajan et al. .

FOREIGN PATENT DOCUMENTS 38541 10/1981 European Pat. Off. .
WO81/01145 4/1981 PCT Int'l Appl. .

OTHER PUBLICATIONS

Chem. Abstr. vol. 97, (1982) 24207b.
Chem. Abstr. vol. 97, (1982) 110388t.
Chem. Abstr. vol. 92, (1980) 164282u.
Chem. Abstr. vol. 95, (1981) 169744t.
Chem. Abstr. vol. 86, (1977) 190462y.
T. E. Fickel et al., Nature, The New Biology 241 161 (1973).
Ponpipom et al., J. Med. Chem. 24 1388 (1981).
B. C. Ames, Proc. Nat. Acad. Sci OSH 70 456 (1973).
H. Kunzek et al., J. Prakt. Chemie, 322 186 (1980).
J. V. Castell et al., Helv. 62 2507 (1979).

Primary Examiner—Delbert R. Phillips
Attorney, Agent, or Firm—William H. Edgerton; Richard D. Foggio; Alan D. Lourie

[57] ABSTRACT

A series of prodrugs is described which have improved antimicrobial activity and physico-chemical properties. The structures of the biologically active ingredients are characterized by having a selected oligopeptide backbone attached, via the α-carbon of an L-alanyl unit thereof, by means of a disulfide link to the residue of an antimicrobial mercaptan.

17 Claims, No Drawings

ANTIMICROBIAL DISULFIDE PRODRUGS

This invention relates to antimicrobial compositions containing, as active ingredients, prodrugs whose structures have a known mercapto-containing antimicrobial residue attached to an oligopeptide chain by means of a disulfide link. Further, this invention concerns methods of producing antimicrobial activity using such prodrugs together with certain new chemical compounds, also useful for using this invention.

BACKGROUND OF THE INVENTION

The prior art recognizes that peptide transport permease systems are one mechanism by which chemical substances are carried through the cell membrane of an antimicrobial organism. Both di- and oligopeptide transport systems are present in the cell membrane, for example, in the cell membrane of *Escherichia coli*, B. C. Ames, Proc. Nat. Acad. Sci. OSH 70 456 (1973), C. Gilvarg, Nature, the New Biology 241 161 (1973).

Peptide transport systems are widespread in both procaryotic and eukaryotic microorganisms. A prodrug which can be transported per se through the cell membrane of such organisms via the permease system and, then, release the drug within the cell would possess enhanced activity.

A number of synthetic derivatives have been prepared which take advantage of these transport systems such as those described by M. M. Ponpipom, et al., J. Med. Chem. 24 1388 (1981), European Patent Office application No. 38,541 or C. Philip et al., PCT application, publication No. WO81/01145. Some of these types of compounds were designed to limit toxicity or to achieve more specific biological activity. Most compounds of the prior art are active, without degradation at the receptor site, in the transport form due to their resistance to intracellular peptidases. In other words, they are not in latentiated form as are the compounds of this invention. For example, the Philip publication, cited above, discloses anti-tumor moieties which are attached by a covalent bond to a polypeptide.

A number of potentially useful chemotherapeutic agents are present in the prior art which are impermeant or poorly permeant to the cell membrane of an infecting organism. The impermeant nature of these compounds may be due to the inherent physico-chemical properties of the compounds or due to an acquired resistance to them in the permease system of the cell membrane of the target species.

Several related United States patents describe compounds which have angiotensin converting enzyme inhibiting activity whose structures have a tripeptide containing a central cysteinyl unit attached to a proline-like ring by means of a disulfide bond, U.S. Pat. Nos. 4,284,624; 4,325,943; 4,325,944 and 4,325,945.

Another series of U.S. patents, U.S. Pat. Nos. 4,237,267 and 4,258,193, disclose a large number of disulfides which are used in exchange reactions, including a few compounds with structures having pyridine N-oxide attached via a disulfide bond to the alanyl unit of an oligopeptide or to alanine itself.

The S-ethylthio protective group has been used, along with others, in procedures to prepare cysteine-containing peptides. The S-ethylthio group was inserted into the peptide structures by displacement of an S-guanylthio moiety by ethylmercaptan in a solvent system of dimethylformamide-triethylamine, H. Kunzek et al., J. Prakt. Chemie, 322 186 (1980).

J. V. Castell et al., Helv. 62 2507 (1979), reported that a mixed cysteine-pyridine disulfide reacted, by displacement, with various mercaptans in acetic acid to form mixed disulfides during a study of the use of 2-pyridine sulfenyl chloride to form protected cysteinyl derivatives.

DESCRIPTION OF THE INVENTION

This invention concerns, as active antimicrobial ingredients, a series of prodrugs whose antibacterial or antifungal activities are enhanced or whose drug delivery capabilities are improved. The active warhead is attached via a disulfide bridge to a specific di- or oligopeptide chain. When the prodrug is placed in contact with a fungal or bacterial target species, the oligopeptide chain enhances absorption of the warhead, or antimicrobial residue, through the peptide transport channels of the cell membrane of the infecting species. Then, within the cell, the prodrug reacts with intracellular sulfhydryl containing compounds, such as glutathione, which are known to be present in the cells to release the active warhead by a disulfide exchange reaction.

The active anti-microbial prodrugs, which are the basis of this invention, must have structures that possess a number of features necessary for them to act as prodrugs having improved properties. The structures, usually, contain an oligopeptide backbone of from 2–6 amino acid units, one of which is, necessarily, a L-alanyl which is β-substituted through a disulfide link with a residue of a known mercaptan antimicrobial agent. This L-alanyl unit is designated as the "carrying" unit of the peptide backbone. The peptide chain must have a free amino group at the N- or amino-terminus, and, preferably, also a free carboxy group at the C- or carboxy-terminus.

The active ingredients of this invention are exemplified by the following structural formula:

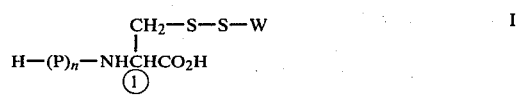

in which:
n is an integer of from 1–5;
P is, individually, alanyl, ornithyl, lysyl or phenylalanyl; and
W is the residue of a compound having antimicrobial activity whose structure contains a mercaptan group (—SH).

The configuration of the C-unit amino acid (1) must be L. The configuration of the adjacent amino acid unit (2) must, likewise, be L. More removed units at positions 3–6 of the backbone oligopeptide may be either D or L or may be other natural amino acids. It should be emphasized that, for convenience, the description of this invention numbers the warhead-carrying amino acid unit as 1 at the carboxy or C-unit of the oligopeptide chain, with numbering proceeding down the chain toward the amino or N terminus. In fact, the carrying unit need not be at a terminal position of the oligopeptide backbone.

More specifically, W is the residue of any antibacterial or antifungal agent whose structure contains a free mercapto radical (—SH). This group of compounds is well known in the art, for example, in European Patent Office application No. 38,541 referred to above, at page 2 line 5 to page 3 line 6. The impermeant or poorly permeant properties of many of the mercaptan containing therapeutic agents is also disclosed in the EPO reference.

The warhead parent compounds (HSW) may range from topical agents such as the 2-mercaptopyridines or alkylmercaptans to systemic agents such as the known 4-[N-(2-mercaptoethyl)]-aminopyridine-2,6-dicarboxylic acid or other cell wall active antibacterials.

The pyridine containing warheads are preferred, for example, those in the literature such as U.S. Pat. Nos. 2,540,218; 3,590,035; 3,700,676, 3,759,932; 3,773,770; 3,968,118; 3,972,888 and German Offen. 2,165,752 (CA 77 126557j).

Species of such compounds are 2-pyridinethiol-N-oxide (pyrithione), 3-methyl-2-pyridinethiol-N-oxide, 3-ethoxy-2-pyridinethiol-N-oxide, 3,5-dichloro-2-mercaptopyridine-N-oxide, 5-chloro-2-mercaptopyridine-N-oxide, 5-bromo-2-mercaptopyridine-N-oxide, 3,4,5,6-tetrachloro-2-pyridinethiol-N-oxide, 6-mercapto-2-picoline-N-oxide, 4-methoxy-2-pyridinethiol-N-oxide, 5-methyl-2-pyridinethiol-N-oxide, 4-dodecylthio-2-pyridinethiol-N-oxide, 4-benzylsulfonyl-2-pyridinethiol-N-oxide, 4-benzylthio-2-pyridinethiol-N-oxide, 4,7-dimethyl-2-pyridinethiol-N-oxide, 1-hydroxy-2-pyridinethione, pyridine-2-thiol.

The pyridyl subgroup of the compounds of formula I is exemplified by the formula in which SW is:

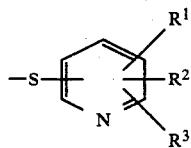
II in which $R^1$, $R^2$ and $R^3$, each, are hydrogen, alkyl of 1-12 carbons, alkoxy of 1-12 carbons, alkylthio of 1-12 carbons, phenoxy, phenylthio, phenylsulfonyl, benzyloxy, benzylthio, carboxy or halo, such as chloro or bromo; or N-oxide derivatives of said compounds.

Said alkyl or alkoxy groups are preferably of 1-2 carbons.

It should be noted that the pyridylthio containing compounds, especially those having the specific pyridylthio or pyridylthio-N-oxide moieties in their structures, also serve as intermediates since these moieties are excellent leaving groups in the disulfide exchange reaction described below.

Other —SW groups of formula I are:

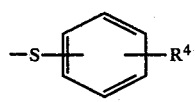
(a)

in which $R^4$ is one or two substituents such as nitro, carboxy, halo, cyano, lower alkyl of 1-6 carbons or lower alkoxy of 1-6 carbons;

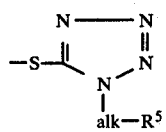
(b)

in which alk is alkylene of 2-6 carbons and $R^5$ is carboxy, sulfonamide, sulfamyl, carbomethoxy, carbamyl.

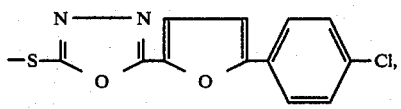
(c)

U.S. Pat. No. 4,134,893;

(d) —S—CH$_2$CH$_2$OH,

CA 90 98007e;

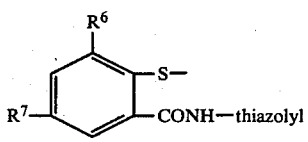
(e)

in which $R^6$ and $R^7$ are hydrogen, chloro or bromo, CA 86 89671v;

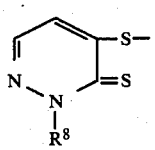
(f)

in which $R^8$ is hydrogen, methyl, ethyl, benzyl, U.K. Pat. No. 2,025,416;

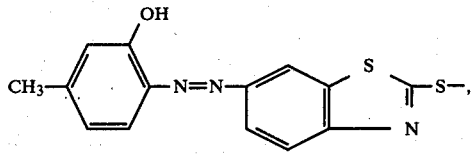
(g)

CA 93 150163g;

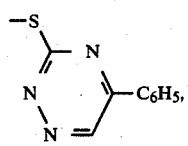
(g)

CA 94 185507c;

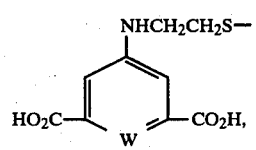
(h)

(i) —S—alk in which alk has from 1-12 carbons.

(j) —SCH$_2$CO$_2$H

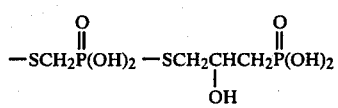
(k)

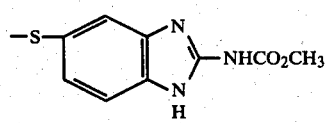
(l)

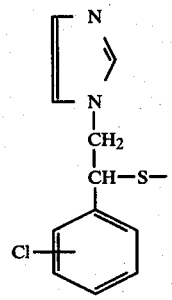
(p)

The active ingredients of formula I are prepared by the following reaction sequence:

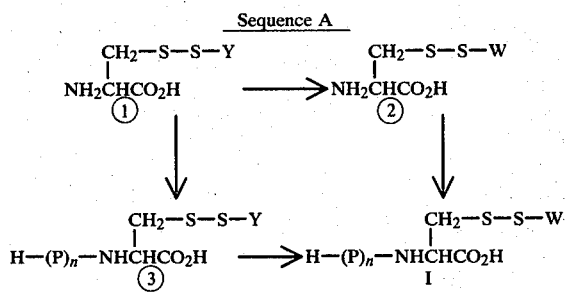

In reaction Sequence A, n, P and W are as defined above for formula I. Y is a chemically displaceable or leaving group, when taken with the adjacent S; for example, pyridyl, pyridyl-N-oxide, and guanyl.

The key reaction is a disulfide exchange between a mixed disulfide and the warhead mercaptan (HSW). The mixed disulfide has a readily displaceable thio containing group (—S—Y) S-connected to the β-alanyl unit itself (1) or to the oligopeptide containing the β-alanyl unit (3). The reaction is most conveniently run on the amphoteric form of the amino acid or oligopeptide starting material. One skilled in the art will recognize that the reaction can, also, be run on disulfide starting materials having amino or carboxy protecting groups on the oligopeptide chain or on the warhead. These are then removed after the sulfur-sulfur interchange.

The reaction is carried out by combining the mixed disulfide (1 or 3) with a stoichiometric quantity or, preferably, an excess of the warhead mercaptan (HSW) in a solvent in which both are substantially soluble, for example, an organic solvent such as dimethylformamide, dimethylacetamide, dimethylsulfoxide, ethers such as dioxane, ethyl ether or tetrahydrofuran, halogenated solvents such as methylene chloride, chloroform or carbon tetrachloride or esters such as ethyl acetate. Aqueous solvents, preferably at an alkaline pH, can be used if the warhead mercaptan is water soluble.

The course of the reaction is followed by thin layer chromatography using methods described in the working examples. Ambient or room temperature of reaction until substantial completion, from 30 minutes to 12 hours, is very satisfactory. Moderate heat can be, optionally, used for sluggish interchanges. Therefore, in fact, the exchange reaction can be run at temperature chosen from −15° up to about 100°. The desired chemical products of the reaction are isolated by standard means, after removal of any protective groups. Purification by gel filtration over a bead-formed gel prepared by cross-linking dextran with epichlorohydrin ("Sephadex", Pharmacia) is convenient.

The antimicrobial compositions of this invention comprise two sub-groups of dosage units which are used to treat bacterial or fungal infections. The surface infections are the particular targets of the active compounds of formula I. Especially preferred are the active ingredients in which the warhead portion of the oligopeptide prodrug is derived from a pyridylthiol, a thiophenol or an alkyl mercaptan, each group of which are known to the art to have antimicrobial properties. These are not usually used systemically in the prior art because of their toxicity or physico-chemical properties.

The prodrugs of this invention are brought into contact with the infectious species by use of carrier forms such as solutions, emulsions or suspensions for topical use, shampoos, creams, troches, gums, drenches, soaps, dry or wet pressure sprays, bandages, suppositories, powders, and mouth washes. These are prepared as described in Remington's Pharmaceutical Sciences, 13th Edition, 1965 Mack. The concentration of the prodrug will depend on both the inherent activity of the warhead as well as that of the prodrug form which has enhanced cell membrane permeability, taken with the product form and the site of infection. Generally speaking, for topical use, quantities not toxic to the patient but having effective antimicrobial activity are chosen from the range of 0.2–10%, preferably 0.5–4%, by weight.

In addition, the prodrugs of this invention which have efficacy against systemic infections are combined in oral and parenteral dosage units in quantities which are effective against the infecting agents but which are nontoxic to the patient. Parenteral use includes intravenous, intramuscular or infusion administration.

The infectious microbes which are the targets of the prodrug active ingredients of this invention, are any that are known to be susceptible to the warhead, in vivo, as well as those against which the novel increased cell membrane permeability, newly discovered here, makes the warhead active in a practical way. Examples of such organisms are *Escherichia coli, Aspergillus niger, Chetonium globossum, Staphylococcus aureus, Candida albicans, Microsporum canis, Peptococcus acnes, Peptococcus granulosum, Peptococcus saccherolyticus,* various Helminthosporums, *Trichophyton rubrum, Candida tropicalis* or *Cryptococcus neoformans.*

The method of this invention comprises administering the antimicrobial compositions, described above, to a human or animal subject or patient infected with a bacterium or fungus, either topically, orally or parenterally, in a quantity which is nontoxic to the subject but effective against the infecting bacterium or fungus.

Also, part of this invention are new chemical compounds for use as chemical intermediates and topical antimicrobial agents having the structural formula:

III in which:

n is an integer of from 1-5;

$W_1$ is as defined for structural formula II (W) above, and each of the amino acid units of the oligopeptide chain has the L-configuration.

Preferred compounds of this subgroup are those of formula III in which n is 1-3. Another such group have structures where $W_1$ is 2-pyridyl, 2-pyridyl-1-one, methyl-2-pyridyl or methyl-2-pyridyl-1-one.

Advantageous compounds of this invention are those of structural formula III and the preferred group in which n is 1.

A second group of new chemical compounds of this invention are those having the structural formula:

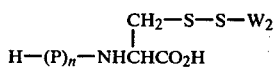     IV in which:

n and P are as defined for formula I above;

$W_2$ is 2,6-dicarboxy-pyridyl-4-aminoethyl;

and each of the amino acid units of the oligopeptide chain is of the L-configuration.

The reactions, outlined above, are described to be carried out in liquid phase, however, as with most peptide reactions, solid phase or enzyme technology may be used on certain of these as will be known to the art, R. B. Merrifield, Biology 3 1385 (1964) or J. Am. Chem. Soc, 85 2149 (1963).

Also, one skilled in the art will recognize that any groups present in the peptide chain or in the warhead W which may be chemically reactive under the conditions of reaction sequence A or the earlier reactions should be protected, as known to the art, U.S. Pat. No. 3,803,120 or EPO Application No. 38,541 or U.S. Pat. No. 3,957,803.

While the prodrugs of this invention are most useful in treating bacteria or fungus microbes topically, or even systemically in a whole animal, the same prodrug concept can be used for other purposes. If the warhead, W, is a known compound having other pharmacodynamic properties, the oligopeptide prodrug can be used to increase cell membrane permeability or to improve distribution or absorption of drug. In other instances, the oligopeptide prodrug can be used to prepare new pharmaceutical forms such as injectable preparations of compounds not readily useful for such uses because of their physico-chemical properties such as low solubility. These utilities may be applied to other mercaptan containing drugs such as penicillamine, thiopental, propylthiourea, 6-mercaptopurineriboside, 6-thioguanine, 6-mercaptopurine, N-acetylcysteine or N-(2-methyl-3-thiopropionyl)-proline.

The prodrugs of formula I are represented herein as their amphoteric polypeptide forms. One skilled in the art will recognize that salt forms of the prodrugs may be equally useful, such as pharmaceutically acceptable acid addition salts when a basic center is present in the polypeptide chain or in the carried warhead. Alternatively, pharmaceutically acceptable basic salts derived from the usual bases, such as those having alkali metal or nontoxic organic amine cations, can be prepared if an acid center is present. Both types of salts are prepared as known to the art, usually by contacting the prodrug with an excess of acid or base in a suitable solvent.

The following examples are designed to teach the practice of this invention as well as the biological activity of representative compounds of this invention. Other variations of the structures of formula I will be apparent to those skilled in the art, such as using a L-homocysteine carrying unit, rather than the cysteine unit used to illustrate this invention. These variations offer little advantage over the invention as described herein. All temperature are in degrees Centigrade. T.l.c. refers to thin layer chromatography. NMR refers to nuclear magnetic resonance spectrum. MPLC refers to medium pressure liquid chromatography.

EXAMPLE 1

S-Ethylthiocysteine (497 mg, 2.75 mm, m.p. 180°, lit. 199°-200°) was dissolved in 10 ml of water, followed by 270 mg (2.5 mm) of sodium bicarbonate. The mixture was cooled to 0°, at which temperature, 2.5 ml of 1 N sodium hydroxide solution was added, along with 6 ml of acetonitrile and a solution of 380 mg (3.3 mm) of alanine N-carboxyanhydride (Leuch's anhydride, The Peptides, E. Grossand and J. Meienhofer, Academic Press, page 85) in 2 ml of acetonitrile. After standing at room temperature for 3 hours, the pH was adjusted to 5.5 with 3 N hydrochloric acid. The mixture was evaporated to give an impure solid which was treated with water to separate the water soluble material which was purified by medium pressure reverse phase chromatography over silica gel, eluting, first, with water followed by 5% methanol, 10% methanol and 25% methanol. The four fractions were homogeneous by thin layer chromatography. They were combined and lyophilized to give 0.35 g (50%) of L-alanyl-S-ethylthiocysteine; NMR spectrum ($D_2O$+1 drop DCl, ppn) 3.2(t), 2.8(g), 1.6(d), 1.3(t).

Anal. Calcd. for $C_8H_{16}O_3N_2O_3S_2.\frac{1}{2}H_2O$: C, 36.77; H, 6.56; N, 10.72. Found: C, 37.14; H, 6.56; N, 10.72.

EXAMPLE 2

A mixture of 3.02 g of L-cysteine and 75 ml of glacial acetic acid was added slowly to a mixture of 11.0 g of 2,2'-dipyridyldisulfide and 75 ml of glacial acetic acid. The precipitated solid was removed. The filtrate was diluted with 600 ml of ethyl ether to separate 3.7 g of β-L-alanyl 2-pyridyl disulfide.

Phosgene was passed through a mixture of 0.5 g of L-alanine and 20 ml of dry tetrahydrofuran with stirring and refluxing. After 2 hours, the clear solution was cooled and concentrated. The residue, 0.41 g of alanyl N-carboxyanhydride, was recrystallized from toluene.

A mixture of 0.68 g (2.97 mm) of the disulfide, 0.30 g of sodium carbonate, 3.0 ml of 1 N sodium hydroxide solution, 12 ml of water and 12 ml of acetonitrile was cooled to −10°. An excess of alanyl N-carboxyanhydride was added, dissolved in 7 ml of acetonitrile. The mixture was stirred at 0° for 3 hours. The liquid phases were separated. The aqueous layer was taken to pH 7 with a few drops of sulfuric acid. Ethanol was added. Sodium sulfate was removed by filtration. The filtrate was evaporated. Ethanol was added and the resulting solid was 0.194 g of L-alanyl-β-L-alanyl 2-pyridyl disulfide which was purified twice over a reverse phase column as described above, with elution, first with water, 10% methanol and 50% methanol and, then, the second time with 50% methanol to give 23 mg of product which was pure by thin layer chromatography.

Anal. Calcd. for $C_{11}H_{14}N_3O_3S_2.Na.\frac{3}{4}H_2O$: C, 39.22; H, 4.64; N, 12.47. Found: C, 39.03; H, 4.98; N, 12.27.

EXAMPLE 3

A mixture of 0.47 g (1.91 mm) of L-alanyl N-oxy-2-pyridyl disulfide, prepared as in Example 2 using pyrithione as the mercapto starting material, 0.191 g of sodium carbonate, 1.91 ml of 1 N sodium hydroxide solution, 8 ml of water and 8 ml of acetonitrile at 0° was reacted for 3 hours with 0.26 g (2.3 mm) of L-alanyl-N-carboxyanhydride dissolved in acetonitrile. The mixture was worked up as described in Example 2 using thin layer chromatography (t.l.c.) over cellulose plates with methanol-saline as developing solvents and ninhydrin or ultraviolet light as markers for following the reaction. Purification was by gel filtration ("Sephadex" G-10) and, then, by a reverse phase medium pressure cellulose column to give 37 mg of the desired, L-alanyl-$\beta$-L-alanyl N-oxy 2-pyridyl disulfide.

Anal. Calcd. for $C_{11}H_{15}N_3O_4S_2 \cdot 2H_2O$: C, 37.38; H, 5.42; N, 11.89. Found: C, 37.06; H, 4.99; N, 11.50.

This material (2 g) is mixed with 10 g of titanium oxide, 1 g of oxide coloring agents, 7 g of oxyethylenated stearyl alcohol and 6 g of polyglycol stearate, with water added to make 100 g of 2% cream which is applied to the infected body surface.

EXAMPLE 4

A solution of 0.77 g (6.7 mm) of L-alanyl-N-carboxy anhydride in 10 ml of acetonitrile was added at $-10°$, with stirring, to a mixture of 2.0 g (6.1 mm) of $\beta$-L-alanyl 2-pyridyl disulfide, prepared as in Example 2, 0.61 g of sodium carbonate, 6.1 ml of 1 N sodium hydroxide, 25 ml of water and 31 ml of acetonitrile. The reaction was continued for two hours in the cold. The phases were separated. The aqueous phase was washed once with 20 ml of cold acetonitrile and, then, heated to 40° for 5 minutes.

The resulting solution was mixed with 12 ml of water, 31 ml of acetonitrile and 2.45 ml of 1 N sodium hydroxide (pH~9). After cooling to $-10°$, a solution of 0.77 g (6.7 mm) of L-alanyl-N-carboxyanhydride in 10 ml of acetonitrile was added. The resulting mixture was reacted in the cold for 2 hours. The aqueous layer was washed with cold acetonitrile, then, adjusted to pH 5.85 with sulfuric acid. Ethanol was added to separate inorganic salts. The filtrate was evaporated to leave a residue which was dissolved in 10 ml of water which solution was, again, diluted with ethanol. The filtrate was concentrated. The residue was taken up in water and lyophilized to give 1.05 g of product.

This material (200 mg) was separated into three products using reverse phase medium pressure liquid chromatography over a cellulose column using 1:1 5% salt solution:methanol. In order of elution, the dipeptide (43 mg), tripeptide (19 mg) and tetrapeptide (11 mg) were obtained. The separation was repeated on 0.82 mg of mixture to give analytical samples:

(a) L-alanyl-$\beta$-L-alanyl 2-pyridyl disulfide identical to that previously described.

(b) L-alanyl-L-alanyl-$\beta$-L-alanyl 2-pyridyl disulfide
Anal. Calcd. for $C_{14}H_{20}N_4O_4S_2 \cdot H_2O$: C, 43.06; H, 5.68; N, 14.34. Found: C, 42.88; H, 5.60; N, 14.51.

(c) L-alanyl-L-alanyl-L-alanyl-$\beta$-L-alanyl 2-pyridyl disulfide
Anal. Calcd. for $C_{17}H_{25}N_5O_5S_2 \cdot \frac{1}{2}H_2O$: C, 45.12; H, 5.79; N, 15.47. Found: C, 45.43; H, 5.78; N, 14.84.

EXAMPLE 5

A mixture of 3.0 g (11.2 mm) of 5-thioguanylcysteine and 50 ml of dry dimethylformamide was cooled to $-15°$, then, mixtures of 1.11 g (10 mm) of 2-mercaptopyridine and 15 ml of dimethylformamide as well as 3.03 g (30 mm) of triethylamine in 15 ml of dimethylformamide were added, separately, with stirring. The mixture was allowed to warm to room temperature and was stirred for 1 hour. The mixture was filtered. The solid residue was washed with methylene chloride, methanol and ether to give 1.12 g (43%) of $\beta$-L-alanyl 2-pyridyl disulfide. This material (500 mg) is reacted with D,L-phenylglycyl-N-carboxyanhydride, as described above, to give D,L-phenylglycyl-$\beta$-L-alanyl 2-pyridyl disulfide.

EXAMPLE 6

A mixture of 0.83 g (2.5 mm) of di-tert.-boc-ornithine, 0.54 g (2.5 mm) of N,N'-disuccinamidyl carbonate [H. Ogura, Tetrahedron Letters 49 4745 (1969)], 0.20 g (2.5 mm) of pyridine and 15 ml of acetonitrile was stirred overnight at room temperature. The solvent was evaporated. The residue was dissolved in ethyl acetate which extract was washed with water, brine, then concentrated, after drying, to give 0.98 g (91%) of di-tert.-boc-L-ornithine, N-hydroxysuccinimide ester.

The activated ester (1.87 g, 4.35 mm) in 26 ml of dioxane was added to another mixture of 2.06 g (4.79 mm) of $\beta$-L-alanyl 2-pyridyl disulfide hydrochloride, 1.10 (13.05 mm) of sodium carbonate and 22 ml of water. The resulting mixture was stirred at room temperature for 5 hours. The solvent was evaporated. The residue was dissolved in water (pH~8.3) and the extract washed with ethyl acetate. The aqueous layer was taken to pH 3.5 with 10% citric acid, then, extracted with ethyl acetate. The acid phase layer was washed with citric acid solution and brine, then, dried and concentrated in vacuo to give 1.83 g of residue which demonstrate the desired product plus impurities by t.l.c. analysis carried out as described above. The residue was purified over a silica column by medium pressure liquid chromatography using methylene chloride, 2% methanol in chloroform and 5% methanol in methylene chloride. The desired product was eluted by the last solvent system (0.742 g). After a further purification over a reverse phase column, 0.60 mg of di-tert.-butoxycarbonyl-L-ornithyl-$\beta$-L-alanyl 2-pyridyldisulfide was obtained, pure by t.l.c.

A 10 ml portion of glacial acetic acid was saturated with hydrogen bromide with cooling. The t.-boc dipeptide sulfide (100 mg) was added. After stirring for 2 hours, the solvent was evaporated. The residue was triturated several times with ether, filtered and dried to give 0.098 g of L-ornithyl-$\beta$-L-alanyl 2-pyridyl sulfide, pure by t.l.c. analysis using butyl alcohol, acetic acid, water over cellulose.

EXAMPLE 7

A mixture of 0.301 (1.0 mm) of L-alanyl-$\beta$-L-alanyl 2-pyridyl disulfide, prepared as in Example 4, 5 ml of water and 0.168 g (2.0 mm) of sodium bicarbonate was combined with a solution of 0.43 g (1.0 mm) of di-t.-boc-L-ornithine, N-hydroxy succinimide ester, prepared as in Example 6, in 6 ml of dioxane. Stirring the reaction mixture at room temperature for 3 hours completed the reaction, as noted by t.l.c. analysis using 1:1 5% brine/methanol. The solvent was evaporated. The residue was diluted with 13 ml of water. The mixture was cooled in an ice bath and the pH adjusted to 4 with 10% citric acid solution, while layered with ethyl acetate. The organic layer was separated and combined with two further ethyl acetate wash layers. The combined and dried organic extracts were concentrated to give 0.536 of the di-t.-boc-L-ornithyl-L-alanyl-β-L-alanyl 2-pyridyl disulfide. T.l.c. demonstrated one spot, using silica gel plates and a 90:10:3 methylene chloride/methanol/formic acid solvent system.

The t.-boc-peptide (100 mg) was combined with 1 ml of anisole and 1 ml of trifluoroacetic acid cooled in an ice bath. T.l.c., using the described procedure, indicated reaction was complete at 2 hours, with stepwise removal of the N-protective groups. The mixture was poured into 40 ml of ether with stirring. The solid was separated, washed with ether and dried to give 87 mg of L-ornithyl-L-alanyl-β-L-alanyl 2-pyridyl disulfide.

The preparation was run as described on 4 times larger scale to give 0.357 of impure tripeptide disulfide. This was dissolved in water and stirred with a weakly basic anion exchange column in free base form (IR-45). The filtrate was adjusted to pH 8.8 with 1 N lithium hydroxide, then, lyophilized to give 0.416 g of L-ornithyl-L-alanyl-β-L-alanyl 2-pyridyl disulfide. This material was taken over a reverse phase medium pressure liquid chromatographic column to give the desired tripeptide.

Anal. Calcd. for $C_{16}H_{25}N_5O_4S_2 \cdot 3H_2O$: C, 40.92; H, 6.65; N, 14.91. Found: C, 40.90; H, 6.91, N, 14.80.

The reactions described above are used to prepare L-lysyl-L-alanyl-β-L-alanyl 2-pyridyl disulfide and D,L-lysyl-L-alanyl-β-L-alanyl 2-pyridyl disulfide.

A dermatological cake is prepared by mixing 2 g of L-ornithyl-L-alanyl-β-L-alanyl 2-pyridyl disulfide with 23 g of lanolin and 75 g of esters of sodium iso-thionate and fatty acids ("Igepon" A).

EXAMPLE 8

L-Alanyl-L-alanyl-β-L-alanyl 2-pyridyl disulfide (15.3 mm, prepared as described above) and 4-[N-2-mercaptoethyl)]amino-pyridine-2,6-dicarboxylic acid (15.8 mm) were dissolved in a solution of 0.1 M dipotassium hydrogen phosphate buffer (~4 ml). After 5 minutes at room temperature, the reaction mixture was applied to a gel column ("Sephadex" G-13, 41×1.3 cm) which had been equilibrated with 1.01 M acetate buffer at pH 4. The product is eluted with the same buffer. The fractions were analyzed by paper strip chromatography using the ninhydrin test. Fractions 27–42 were combined, evaporated to dryness under reduced pressure to give a residue which was dissolved in 0.2 ml of distilled water. Acetate was removed by gel filtration to give L-alanyl-L-alanyl-β-L-alanyl 2-(2,6-dicarboxy-pyridyl-4)-aminoethyl disulfide.

This material (500 mg per dosage unit) is dissolved in saline and infused into a patient in need of antimicrobial treatment.

EXAMPLE 9

The $R_f$'s of representative compounds prepared by the methods described above were determined by descending chromatography on Whatman no. 1 paper using butyl alcohol/water/acetic acid (4:1:4 upper layer) as solvent with staining by ninhydrin and Zahn's reagent to give the following results:

| Peptide | 2-mercapto-pyridine | N—[4-(2-mercaptoethyl]-amino-pyridine-2,6-dicarboxylic acid |
|---|---|---|
| L-Ala—β-L-alanyl-S— | 0.7 | 0.15 |
| L-Ala—L-ala-β-L-ala-S— | 0.6 | 0.21 |
| L-Orn—L-ala-β-L-ala-S— | 0.47 | 0.13 |

EXAMPLE 10

Following is a general procedure for preparing the mixed oligopeptide warhead disulfides which are the active ingredients of this invention:

A solution of L-alanyl-β-L-alanyl 2-pyridyl disulfide (1 mm) in 30 ml of dimethylformamide is cooled to −15°, under a stream of nitrogen. To this solution is added a solution containing the selected mercaptan, WSH, (1 mm), triethyl amine (1 mm) and 10 ml of dimethylformamide. After the addition is complete, the reaction mixture is stirred at −15° C. for 30 minutes and for 60 minutes at room temperature. The reaction mixture is concentrated. The residue is dissolved in water and the solution is, then, extracted with ethyl acetate. The aqueous phase is concentrated to leave the desired product which is purified by either reverse phase medium pressure chromatography using a $C_{18}$ modified silica gel column and a 20% aqueous methanol eluent or by passage down a gel column ("Sephadex" G-10) as described above. Each of the mercaptans listed above is used in this procedure to prepare the selected disulfide prodrug.

EXAMPLE 11

In addition to the antimicrobial compositions described above, the following methods are used:
Percentages are by weight:
A. Clear solution:

| Water | 97.5% |
|---|---|
| Disulfide | 2.5% |

B. Powder for solution:

100 Ml of a solution of the selected disulfide in saline (3%) is lyophilized to give a solid which is analyzed and placed in a multidose vial for reconstitution.

C. Powder:

| Talc | 99 g |
|---|---|
| Glyceryl oleate | 3 g |
| Isopropyl nyristate | 7 g |
| Disulfide | 3 g |
| Perfume | 2 cc |

D. Suppository:

Cocoa butter (2 g) is mixed with 0.05 g of disulfide. The mixture is melted and poured into a mold.

E. Tincture:

| Disulfide | 1% |
|---|---|
| Ethanol | 20% |
| Propylene glycol | 10% |
| Water | 69% |

ANTIMICROBIAL EXAMPLE

A. Disc assay for inhibition by various compounds on seeded agar plates

The medium was that of Davis and Mingioli, supplemented with 4 μg/ml of thiamine and 50 μg/ml of required amino acid supplements with 1.5% agar for solid media. Seeded agar plates contained 0.1 ml of an overnight culture per 20 ml of molten agar (kept at 49°) containing appropriate supplements.

1-20 ml of test solution was added to ¼" diameter paper discs and the discs placed on the surface of agar plates which were incubated overnight at 37°. The bacterial strains of *E. coli*, whose strains are given hereafter, were obtained from the *E. coli* Genetic Stock Center.

B. Inhibition of growth of *E. coli* CB64recA/F'123 by 2-mercaptopyridine (2-MP) and peptide synthons Zones of inhibition on seeded agar plates after overnight incubation.

| | Zone of inhibition diameter, nm | | |
|---|---|---|---|
| nmol | 2-MP | L-Ala—L-Ala—S—2MP | L-ala-L-Ala—L-ala- S—2MP |
| 40 | — | — | ( ) |
| 200 | — | — | 14 |
| 800 | (10–11) | 15 | 25 |

— = no inhibition
( ) = partial zone, but showing significant growth inhibition
ND = not determined

C. Inhibition of growth of *E. coli* CB64recA/F'123 by cysteinyl peptides containing disulphide linked 4-[N-(2-mercaptoethyl)]-amino-pyridine-2,6-dicarboxylic acid (MEPDA) via the β-carbon of the C-terminal L-alanyl unit Zones of inhibition on seeded agar plates after overnight incubation.

| | Zones of inhibition diameter, nm | |
|---|---|---|
| nmol | L-Ala—L-Ala—S—MEPDA | Orn—L-Ala—S—MEPDA |
| 40 | — | ND |
| 200 | — | ND |
| 800 | — | ND |
| 250–500 | ND | (13) |
| nmol | L-Ala—L-Ala—L-Ala—S—MEPDA | Orn—L-Ala—L-Ala—S—MEPDA |
| 40 | (9) | — |
| 200 | 16 | (10) |
| 800 | 24 | (12) |
| 250–500 | ND | ND |

D. Inhibition of growth of *E. coli* CB64recA/F'123 by mixtures of thialysine and tripeptides containing disulphide-linked 4-[N-(2-mercaptoethyl)]-amino-pyridine-2,6-dicarboxylic acid (MEPDA)

| | Zone of inhibition diameter, nm | |
|---|---|---|
| nmol | Orn—L-Ala—L-Ala—S—MEPDA | Orn—L-Ala—L-Ala—S—MEPDA + Thialysine* |
| 80 | — | 11 |
| 160 | — | 14 |
| 320 | — | 16 |
| nmol | L-Ala—L-Ala—L-Ala—S—MEPDA | L-Ala—L-Ala—L-Ala—S—MEPDA + Thialysine* |
| 6 | — | 10 |
| 30 | (11) | 14 |
| 60 | (15) | 18 |

*0.5 μg thialysine was used (a sub-inhibitory concentration)

E. Fungal activity

L-Alanyl-β-L-alanyl-1-oxy-2-pyridyldisulfide had generally less activity in vitro than did 2-mercaptopyridyl-1-one in non-latentiated form but had advantageous physical characteristics such as a lower potential for irritation. For example, disk activity against *Candida albicans* β311 for the prodrug was 0.04 minimal inhibitory concentration with 0.01 for the warhead alone.

What is claimed is:

1. An antimicrobial composition comprising an antimicrobially effective and nontoxic quantity of a compound of the structural formula:

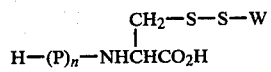

in which:
n is an integer of from 1–5;
P is, individually, alanyl, ornithyl, lysyl or phenylalanyl; and
W is a residue of an antimicrobial mercaptan, said compound having the L-configuration at the carrying C-unit; or a salt thereof with a pharmaceutically acceptable acid or base; combined with an antimicrobial carrier thereof.

2. The composition of claim 1, in which the peptide unit adjacent to the carrying C-unit has the L-configuration.

3. The composition of claim 1 in which the composition is adapted for topical administration.

4. The composition of claim 1 in which the composition is adapted for topical administration and said compound is present in a quantity chosen from the range of 0.2–10% by weight.

5. The composition of claims 1, 3 or 4 in which P is L-alanyl.

6. The composition of claims 1, 3 or 4 in which P is L-alanyl, n is 1 and W is a pyridyl.

7. The composition of claims 1, 3 or 4 in which P is L-alanyl, n is 1 and W is 2-pyridyl.

8. The composition of claims 1, 3 or 4 in which p is L-alanyl, n is 1 and W is 2-pyridyl-N-oxide.

9. The composition of claims 1, 3 or 4 in which P is L-alanyl, n is 2 and W is:

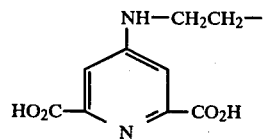

10. The composition of claim 1 in which P is L-ornithyl and n is 1.

11. The composition of claim 1 in which H-(P)$_n$-is L-ornithyl-L-alanyl.

12. A chemical compound of the structural formula:

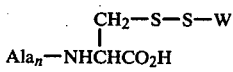

in which:
n is an integer of 1–5; and
W is a pyridyl, each unit of the oligopeptide chain having the L-configuration; or salt thereof with a pharmaceutically acceptable salt or base.

13. The compound of claim 12 in which n is 1–3 and W is 2-pyridyl and the compound is present as the zwitterion.

14. The compound of claim 12 in which n is 1 and W is 2-pyridyl-N-oxide and the compound is present as the zwitterion.

15. A chemical compound of the structural formula:

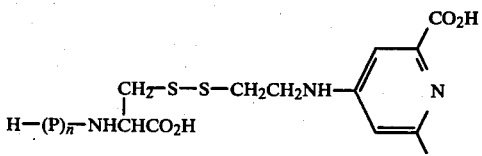

in which:
n is an integer of from 1–5;
P is, individually, alanyl, ornithyl, lysyl or phenylalanyl; said compound having the L-configuration at the carrying C-unit, or a salt thereof with a pharmaceutically acceptable acid or base.

16. The compound of claim 15 in which P is L-alanyl.

17. The compound of claim 15 in which H-(P)$_n$-is L-ornithyl-L-alanyl.

* * * * *